United States Patent
Mizushima et al.

(10) Patent No.: US 8,431,614 B2
(45) Date of Patent: Apr. 30, 2013

(54) LOXOPROFEN DERIVATIVE AND PHARMACEUTICAL PREPARATION CONTAINING THE SAME

(75) Inventors: Toru Mizushima, Kumamoto (JP); Masami Ohtsuka, Kumamoto (JP); Yoshinari Okamoto, Kumamoto (JP); Naoki Yamakawa, Tokyo (JP)

(73) Assignees: LTT Bio-Pharma Co., Ltd., Tokyo (JP); National University Corporation Kumamoto University, Kumamoto-shi, Kumamoto (JP)

( * ) Notice: Subject to any disclaimer, the term of this patent is extended or adjusted under 35 U.S.C. 154(b) by 35 days.

(21) Appl. No.: 13/148,566

(22) PCT Filed: Feb. 18, 2010

(86) PCT No.: PCT/JP2010/052463
§ 371 (c)(1),
(2), (4) Date: Oct. 10, 2011

(87) PCT Pub. No.: WO2010/098251
PCT Pub. Date: Sep. 2, 2010

(65) Prior Publication Data
US 2012/0016158 A1   Jan. 19, 2012

(30) Foreign Application Priority Data
Feb. 26, 2009   (JP) .................. 2009-043801

(51) Int. Cl.
*A61K 31/192*   (2006.01)
*C07C 59/48*   (2006.01)
*C07C 59/86*   (2006.01)

(52) U.S. Cl.
USPC ..................... 514/570; 562/459; 562/468

(58) Field of Classification Search .................. None
See application file for complete search history.

(56) References Cited

U.S. PATENT DOCUMENTS

| | | | |
|---|---|---|---|
| 4,161,538 A | 7/1979 | Terada et al. | |
| 4,407,823 A | 10/1983 | Kirsch et al. | |
| 5,434,292 A * | 7/1995 | Saita et al. ............ | 560/51 |

FOREIGN PATENT DOCUMENTS
JP   53135958 A   11/1978

OTHER PUBLICATIONS

International Search Report mailed Mar. 30, 2010 issued in PCT Application No. PCT/JP2010/052463 filed Feb. 18, 2010.

* cited by examiner

*Primary Examiner* — Paul A Zucker
(74) *Attorney, Agent, or Firm* — Drinker Biddle & Reath LLP (57) ABSTRACT

There is provided a novel loxoprofen derivative that has no side effect such as a gastrointestinal disorder and also has excellent anti-inflammatory and analgesic effects and is represented by the following formula (I) or (II):

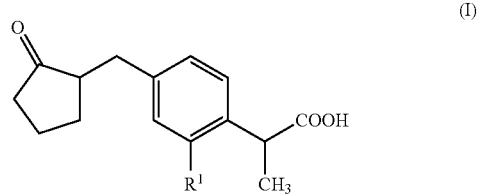

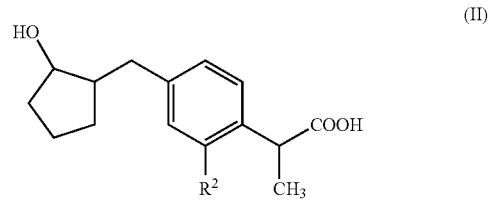

(wherein $R^1$ and $R^2$ each represent a halogen atom or a substituted or unsubstituted phenyl group) or a pharmacologically acceptable salt thereof. In the derivative, the halogen atom is selected from a chlorine atom, a bromine atom, a fluorine atom, and an iodine atom, and a substituent of the substituted phenyl group is a halogen atom, a hydroxyl group, a substituted or unsubstituted lower alkyl group, a lower alkylthio group, a lower alkoxy group, a nitro group, an amino group, or a carboxyl group.

6 Claims, 3 Drawing Sheets

LOXOPROFEN DERIVATIVE AND PHARMACEUTICAL PREPARATION CONTAINING THE SAME

CROSS REFERENCE TO RELATED APPLICATIONS

This application is a National Stage of International Application No. PCT/JP2010/052463 filed Feb. 18, 2010, and which claims benefit of Japanese Patent Application No. 2009-043801 filed Feb. 26, 2009, which are incorporated herein in their entirety.

TECHNICAL FIELD

The present invention relates to novel loxoprofen derivatives that have an excellent antiphlogistic effect and a high level of safety. Specifically, the present invention relates to a loxoprofen derivative that has no side effect, particularly such as a gastrointestinal disorder, and is useful as a pharmaceutical preparation.

BACKGROUND ART

A sodium salt hydrate of loxoprofen (generic name: loxoprofen sodium hydrate) has been widely used clinically as a pharmaceutical preparation that has excellent analgesic, anti-inflammatory, and antipyretic effects.

Various kinds of derivatives that retain the excellent analgesic, anti-inflammatory, and antipyretic effects of loxoprofen have been proposed many times so far. For example, derivatives represented by the following formulae A, B, and C are known (Patent Literatures 1 to 3).

[Chemical Formula 1]

Specifically, Patent Literature 1 discloses the compound represented by the above-mentioned formula (A). This compound is reported to have anti-inflammatory, analgesic, and antipyretic effects. Patent Literature 2 also discloses a wide range of derivatives represented formally by the above-mentioned formula (B). However, these derivatives are different from loxoprofen derivatives provided by the present invention.

Furthermore, Patent Literature 3 discloses a wide range of derivatives represented formally by the above-mentioned formula (C). It is reported that these derivatives have an even more potent anti-inflammatory effect and an even more potent analgesic effect than pre-existing acidic nonsteroidal antiphlogistics (acid NSAIDs) represented by aspirin or indomethacin and have very few side effects such as a gastrointestinal tract disorder.

However, specific severity of the side effects such as a gastrointestinal disorder varies depending on respective pharmaceutical preparations, and the severity of injury of the ulcer onset in an alimentary canal, especially in a gastric mucosa, varies greatly.

Therefore, various investigations on the compounds having anti-inflammatory and analgesic effects have been performed so far to separate their pharmacological effects from their side effects. However, no particular achievement has been produced yet.

Under the above-mentioned circumstances, the present inventors investigated loxoprofen derivatives and successfully synthesized a compound that had excellent anti-inflammatory and analgesic effects while avoiding side effects such as a gastrointestinal disorder, and thus accomplished the present invention.

CITATION LIST

Patent Literature

Patent Literature 1: Japanese Patent Application Laid-Open No. Sho 58-4699
Patent Literature 2: Japanese Patent Application Laid-Open No. Sho 54-103852
Patent Literature 3: International Publication NO. WO 93/02999

SUMMARY OF INVENTION

Problems to be Solved by the Invention

Therefore, it is an object of the present invention to provide a novel loxoprofen derivative that avoids side effect such as a gastrointestinal disorder and also has excellent anti-inflammatory and analgesic effects.

Means for Solving the Problems

The present invention for solving the above-mentioned problems is a loxoprofen derivative represented by the following formula (I) or (II):

[Chemical Formula 2]

-continued (wherein R¹ and R² each represent a halogen atom or a substituted or unsubstituted phenyl group) or a pharmacologically acceptable salt thereof.

Specifically, the present invention is a loxoprofen derivative or a pharmacologically acceptable salt thereof, wherein the halogen atom represented by R¹ and R² in the above-mentioned formulae (I) and (II) is selected from a chlorine atom, a bromine atom, a fluorine atom, and an iodine atom.

More specifically, the present invention is a loxoprofen derivative or a pharmacologically acceptable salt thereof, wherein a substituent of the substituted phenyl group represented by R¹ in the above-mentioned formula (I) is a halogen atom, a hydroxyl group, a substituted or unsubstituted lower alkyl group, a lower alkylthio group, a lower alkoxy group, a nitro group, an amino group, or a carboxyl group. The present invention is also a loxoprofen derivative or a pharmacologically acceptable salt thereof, wherein a substituent of the substituted phenyl group represented by R² in the above-mentioned formula (II) is a halogen atom or a substituted lower alkyl group.

As another embodiment, the present invention is also a pharmaceutical preparation that contains a loxoprofen derivative represented by the above-mentioned formula (I) or (II) or a pharmacologically acceptable salt thereof as an active ingredient.

Among others, in a particularly preferable embodiment, the present invention is a loxoprofen derivative or a pharmacologically acceptable salt thereof, wherein the substituent R¹ in the above-mentioned formula (I) is a fluorine atom, a bromine atom, a p-hydroxyphenyl group, or a p-aminophenyl group, and a pharmaceutical preparation that contains such a compound as an active ingredient.

Advantageous Effects of Invention

The loxoprofen derivative provided by the present invention is a novel compound that has been unknown until now. Furthermore, the loxoprofen derivative provided by the invention has no side effect such as a gastrointestinal disorder, which is caused by conventional acid NSAIDs, and moreover has stronger anti-inflammatory and analgesic effects than clinically-used loxoprofen.

Therefore, the loxoprofen derivative provided by the invention is said to be very effective in that it can be used safely in humans due to its wide safety margin.

MODES FOR CARRYING OUT THE INVENTION

As described above, the basic embodiment of the present invention is a loxoprofen derivative represented by the following formula (I) or (II):

[Chemical Formula 3]

(wherein R¹ and R² each represent a halogen atom or a substituted or unsubstituted phenyl group)
or a pharmacologically acceptable salt thereof.

Herein, a halogen atom as a substituent "R¹" or "R²" refers to a halogen atom selected from a chlorine atom, a bromine atom, a fluorine atom, and an iodine atom.

A lower alkyl group that is a substituent of the substituted phenyl group represented by a substituent "R¹" or "R²" refers to a substituted or unsubstituted alkyl group having about 1 to 6 carbon atoms. Specifically, a lower alkyl group refers to a methyl group, an ethyl group, a propyl group, an isopropyl group, a butyl group, an isobutyl group, a sec-butyl group, a tert-butyl group, a pentyl group, an isopentyl group, a hexyl group, or the like.

Substituents of these lower alkyl groups include a hydroxyl group, an amino group, a nitro group, or the like.

A lower alkoxy group refers to a lower alkyloxy group having about 1 to 6 carbon atoms, specifically, a methoxy group, an ethoxy group, a propoxy group, a butoxy group, an isobutoxy group, a sec-butyloxy group, a tert-butyloxy group, a pentyloxy group, an isopentyloxy group, a hexyloxy group, or the like.

Although the positions and the number of substituents of a substituted phenyl group are not particularly limited, the substituted phenyl group is preferably a mono-substituted phenyl group and the substituted position is preferably a meta position or a para position.

Therefore, the following compounds can specifically be listed as novel loxoprofen derivatives provided by the present invention.

[Chemical Formula 4]

$R^1 = F, Cl, Br, I$

[Chemical Formula 5]

$R^{10}$ = p-OH, m-OH,
p-OCF$_3$, p-OCH$_3$,
p-CH$_2$OH, p-NO$_2$,
p-NH$_2$, H, p-CH$_3$,
p-SCH$_3$, p-F,
p-COOH

[Chemical Formula 6]

$R^2$ = F, Br (1,2-cis/1,2-trans)
p-OH—Ph (1,2-cis/1,2-trans)

In the above-mentioned formulae (I-a), (I-b), and (II-a), the configuration of the methyl group on the phenylpropionic acid moiety may be an α-position or a β-position. However, in the present invention, the positions of the methyl groups may be both an α-position and a β-position as well as a mixture thereof.

Furthermore, the hydroxyl group (position 1) and the phenyl group (position 2) of the cyclopentane ring in the formula (II-a) may exist in a cis-configuration or a trans-configuration. In the present invention, the compound of the formula (II-a) may exist in a 1,2-cis form or a 1,2-trans form, or as a mixture of these diastereomers.

Specifically, the novel loxoprofen derivative provided by the present invention may be produced as follows.

It is needless to say that the production method described below is merely one specific production method and the present invention is not limited thereto and that the inventive loxoprofen derivative may be produced by reference to a general chemistry textbook.

Among the loxoprofen derivatives of the present invention represented by the formula (I), the loxoprofen derivative wherein the substituent "$R^1$" is a halogen atom may be synthesized, for example, in accordance with Production Scheme 1 shown in the chemical reaction formula described below.

Production Scheme 1 a: X = F
b: X = Cl
c: X = Br
d: X = I

In the formula, Arabic numerals denote specific compound numbers and Roman numerals denote step numbers in the Production Scheme 1 (this applies to other production schemes described below).

Furthermore, a reaction condition (e.g., reaction time and reaction temperature), a reagent, a solvent, a catalyst, and the like that are used in each production step based on each production scheme described below are intended to exemplify a preferable example of production, and the present invention is not limited to these.

First, commercially available tri-substituted aromatic compounds (1a to 1d) including different halogens were used as a starting material and converted to aldehyde compounds (2a to 2d) by subjecting their amino group ends to a formylation reaction.

Such conversion can be performed, for example, in accordance with the following steps: In step i, a diazotization reaction is performed by using hydrochloric acid/sodium nitrate/copper sulfate/sodium sulfite/sodium acetate. Then, in step ii, the resulting product is treated with hydroximic amine hydrochloride in the presence of paraformaldehyde. Then, in step iii, the resulting product is degraded by using hydrochloric acid to obtain the aldehyde compound of interest.

Then, the obtained aldehyde compounds (2a to 2d) are subjected to, for example, a Wittig reaction using $MeOCH_2P(Ph_3)Cl$ and $C_6H_{18}KNSi_2$ in toluene (step iv), and furthermore, for example, to acid treatment using hydrochloric acid in acetone (step v), thereby obtaining phenyl aldehyde compounds (3a to 3d) that have an extended carbon chain. The phenyl aldehyde compounds (3a to 3d) are converted to phenylacetic acid compounds (4a to 4d) by the oxidation reaction using periodic acid in the presence of 2% by mole of PFC (step vi). Then, the phenylacetic acid compounds (4a to 4d) are converted to phenylacetate ester compounds (5a to 5d) by allowing an esterification reaction of acid and alcohol to occur (step vii).

Furthermore, the obtained phenylacetate ester compounds (5a to 5d) were subjected to an α-methylation reaction using methyl iodide in the presence of about 2 moles of lithium diisopropylamide (LDA) in dry tetrahydrofuran (step viii) and were sequentially converted to propionate ester compounds (6a to 6d). This reaction is preferably performed at a low temperature. For example, it is preferably performed under a temperature range changing gradually from −78° C. to about −40° C.

Subsequently, the propioate ester compounds (6a to 6d) are treated, for example, by reflux with N-bromosuccinimide (NBS) and azoisobutyronitrile (AIBN) in carbon tetrachloride to produce compounds (7a to 7d) having their methyl group ends converted to bromomethylene (step ix). The obtained compounds (7a to 7d) are reacted with methyl 2-oxocyclopentanecarboxylate in the presence of potassium carbonate in a solvent (for example, dry acetone) (step x) to obtain diester compounds (8a to 8d) having a cyclopentane ring as intermediates.

Finally, these intermediate compounds (8a to 8d) are subjected to, for example, acid hydrolysis and decarboxylation using acetic acid/hydrochloric acid, so that, among the loxoprofen derivatives of interest of the present invention represented by the formula (I), loxoprofen derivatives (9a to 9d) wherein the substituent "$R^1$" is a halogen atom are produced.

Furthermore, among the loxoprofen derivatives of the present invention represented by the formula (I), a loxoprofen derivative wherein the substituent "$R^1$" is a substituted or unsubstituted phenyl group may be synthesized, for example, in accordance with Production Scheme 2 or Production Scheme 3 shown in the chemical reaction formulae described below.

Production Scheme 2

[Chemical Formula 8]

10c. X = Br; $R_1$ = Me
11c. X = Br; $R_1$ = Bn

12. $R_1$ = Bn; $R_2$ = p-OH
13. $R_1$ = Bn; $R_2$ = m-OH
14. $R_1$ = Bn; $R_2$ = p-OCF$_3$
15. $R_1$ = Me; $R_2$ = p-OCH$_3$
16. $R_1$ = Me; $R_2$ = p-CH$_2$OH
17. $R_1$ = Me; $R_2$ = p-NO$_2$
18. $R_1$ = Me; $R_2$ = p-NH$_2$

-continued

19. $R_2$ = p-OH
20. $R_2$ = m-OH
21. $R_2$ = p-OCF$_3$
22. $R_2$ = p-OCH$_3$
23. $R_2$ = p-CH$_2$OH
24. $R_2$ = p-NO$_2$
25. $R_2$ = p-NH$_2$

Production Scheme 3

[Chemical Formula 9]

26. $R_2$ = H
27. $R_2$ = p-CH3
28. $R_2$ = p-SCH$_3$
29. $R_2$ = p-F
30. $R_2$ = p-COOMe

31. $R_2$ = H
32. $R_2$ = p-CH3
33. $R_2$ = p-SCH$_3$
34. $R_2$ = p-F
35. $R_2$ = p-COOH

Thus, Production Scheme 2 and Production Scheme 3 illustrate a process for synthesizing loxoprofen derivatives (19 to 25 and 31 to 35) wherein the substituent "$R^1$" is a substituted or unsubstituted phenyl group among the loxoprofen derivatives of the present invention.

First, the carboxylic acid end of the loxoprofen derivative (9c) wherein the aromatic ring is substituted with bromine, which was obtained by Production Scheme 1, was subjected to an esterification of a carboxyl group with methanol or benzyl alcohol (BnOH) in the presence of 4-dimethylaminopyridine (4-DMAP) in 1,2-dichloroethane (step i). Thus, ester-protected compounds (10c and 11c) were synthesized. These compounds were used as substrates for a Suzuki-Miyaura cross-coupling reaction with various boron compounds (step ii) to obtain an ester-protected biphenyl type of loxoprofen derivatives (12 to 17).

The Suzuki-Miyaura cross-coupling reaction can be performed, for example, by using a boron compound [$R_2$—PhB(OH)$_2$] that has the substituent shown as $R_2$ above and treating the reactants by reflux in hydrous tetrahydrofuran with Pd(PPh$_3$)$_4$ in the presence of about 2 moles of sodium carbonate.

For the compound (17) that was substituted by a nitro group at its biphenyl end, the nitro group was converted to an amino group by a reduction reaction using palladium on carbon (Compound 18). Finally, the ester group ends of these compounds (12 to 18) were reduced catalytically or hydrolyzed to obtain the biphenyl type of loxoprofen derivatives (19 to 25) of interest.

Catalytic reduction may be performed, for example, by allowing the compounds to absorb hydrogen gas in an alcohol solvent such as methanol or ethanol with the aid of 10% palladium on carbon. Hydrolysis can be performed by ordinal alkaline hydrolysis (for example, hydrolysis using alkali metal hydroxide in an alcoholic solvent).

On the other hand, different biphenyl-type loxoprofen derivatives (31 to 35) shown in Reaction Scheme 3 were obtained as follows. The diester compound (8c) having a cyclopentanone ring obtained in Reaction Scheme 1 was used as a substrate for the Suzuki-Miyaura cross-coupling reaction with various boronic acid compounds to synthesize diester compounds (26 to 30), which are precursors of the compounds of interest. Finally, these compounds were hydrolyzed and decarboxylated to obtain the different loxoprofen derivatives of interest (31 to 35).

The Suzuki-Miyaura cross-coupling reaction with boronic acid compounds (step i) and the hydrolysis and decarboxylation reaction (step ii) may be performed by using reactions similar to those performed in Reaction Scheme 2 and Reaction Scheme 1 described above.

Furthermore, in the production of reduced loxoprofen derivatives having a cyclopentanol ring represented by the formula (II), which are compounds of interest of the present invention, these derivatives can be synthesized, for example, in accordance with Production Scheme 4 shown in the chemical reaction formula described below.

Production Scheme 4

[Chemical Formula 10]

10a. X = F; $R_1$ = Me
10c. X = Br; $R_1$ = Me
12. X = p-PhOH; $R_1$ = Bn

-continued 36a, c. R₁ = Me
   (1,2-cis, mixture of 4 diastereomers)
37a, c. R₁ = Me
   (1,2-trans, mixture of 4 diastereomers)
38. X = p-PhOH; R₁ = Bn
   (1,2-cis, mixture of 4 diastereomers)
39. X = p-PhOH; R₁ = Bn
   (1,2-trans, mixture of 4 diastereomers)

40a, c. (1,2-cis, mixture of 4 diastereomers)
41a, c. (1,2-trans, mixture of 4 diastereomers)
42. X = p-PhOH
   (1,2-cis, mixture of 4 diastereomers)
43. X = p-PhOH
   (1,2-trans, mixture of 4 diastereomers)

First, carboxylic acid ends of the halogenated loxoprofen derivatives (9a and 9c) produced by the method shown in Production Scheme 1 wherein their aromatic rings are substituted by a fluorine atom or a bromine atom and the biphenyl type of loxoprofen derivative (19) produced by the method shown in Production Scheme 2 that was substituted by a hydroxyl group (para position) at its biphenyl end group were esterified (step i). For example, the carboxyl groups were esterified with methanol or benzyl alcohol (BnOH) in the presence of 4-dimethylaminopyridine (4-DMAP) in 1,2-dichloroethane (step i) to synthesize ester-protected compounds (10c, 11c, and 12).

Then, these compounds were converted to alcohol compounds (36a and 36c; 37a and 37c; 38; and 39), for example, by subjecting them to a reduction reaction using dichloromethan as a solvent and sodium borohydride (step ii) to reduce their carbonyl groups. Finally, the ester group end was reduced catalytically or hydrolyzed (step iii or iv) to obtain reduced loxoprofen derivatives of interest (40a and 40c; 41a and 41c; 42; and 43).

The catalytic reduction or hydrolysis reaction in this case employs means similar to those used in the method of step iv or v in Production Scheme 2.

These compounds and their precursors exist as geometrical isomers in a cis or trans form, which have different configurations at asymmetric carbons at two positions (position 1 and position 2) of the cyclopentane ring in their chemical structures. These compounds and their precursors can be isolated by silica gel chromatography as a mixture of four diastereoisomers, including stereoisomers that have different configurations at each of the asymmetric carbons at α positions.

The loxoprofen derivatives as the compounds of interest of the present invention can be obtained by the production methods described above. The physicochemical properties of the obtained compounds are summarized in the tables 1 to 3 below.

TABLE 1

| No. | property | MS (m/Z) | ¹H-NMR (δ/ppm) |
|---|---|---|---|
| 9a | liquid | 265 M + H⁺ | (CDCl₃)δ: 7.18 (1H, t, J = 7.9 Hz), 6.86 (2H, dd, J = 11.9, 5.4 Hz), 3.98 (1H, q, J = 7.3 Hz), 3.73 (3H, s), 3.68 (3H, s), 3.21 (1H, d, J = 13.9 Hz), 3.02 (1H, d, J = 13.9 Hz), 2.46-2.37 (2H, m), 2.36-2.27 (1H, m), 2.17-2.05 (1H, m), 1.98-1.89 (1H, m), 1.72-1.67 (1H, m), 1.47 (3H, d, J = 7.3 Hz) |
| 9b | liquid | 281 M⁺ | (CDCl₃)δ: 10.79 (1H, brs), 7.32 (1H, brs), 7.21-7.12 (2H, m), 3.69 (1H, q, J = 7.2 Hz), 3.28 (1H, dd, J = 13.7, 4.2 Hz), 2.59 (1H, dd, J = 13.7, 9.7 Hz), 2.51-2.32 (2H, m), 2.21-1.94 (3H, m), 1.82-1.68 (1H, m), 1.62-1.46 (1H, m), 1.50 (3H, d, J = 7.3 Hz) |
| 9c | liquid | 347 M + Na⁺ | (CDCl₃)δ: 7.39 (1H, d, J = 1.5 Hz), 7.25 (1H, d, J = 8.1 Hz), 7.10 (1H, dd, J = 8.1, 1.5 Hz), 4.24 (1H, q, J = 7.2 Hz), 3.10 (1H, dd, J = 13.7, 3.8 Hz), 2.47 (1H, dd, J = 13.7, 9.3 Hz), 2.40-2.27 (2H, m), 2.18-1.93 (3H, m), 1.83-1.67 (1H, m), 1.60-1.54 (1H, m), 1.50 (3H, d, J = 7.2 Hz) |
| 9d | liquid | 373 M + H⁺ | (CDCl₃)δ: 7.68 (1H, s), 7.25 (1H, d, J = 6.6 Hz), 7.14 (1H, d, J = 8.4 Hz), 4.13 (1H, q, J = 7.2 Hz), 3.08 (1H, dd, J = 13.6, 3.7 Hz), 2.44 (1H, dd, J = 13.7, 9.3 Hz), 2.37-2.26 (2H, m), 2.18-2.06 (2H, m), 2.03-1.94 (1H, m), 1.83-1.67 (1H, m), 1.59-1.42 (1H, m), 1.47 (3H, d, J = 7.3 Hz) |
| 19 | white solid | 338 M⁺ | (CD₃OD)δ: 7.28 (1H, d, J = 8.1 Hz), 7.15-7.10 (3H, m), 6.99 (1H, s), 6.82 (2H, d, J = 8.6 Hz), 3.85 (1H, q, J = 7.0 Hz), 3.05 (1H, dd, J = 13.6, 3.8 Hz), 2.52 (1H, dd, J = 13.6, 9.4 Hz), 2.45-2.24 (2H, m), 2.14-2.02 (2H, m), 1.99-1.89 (1H, m), 1.82-1.69 (1H, m), 1.67-1.51 (1H, m), 1.27 (3H, d, J = 7.0 Hz) |
| 20 | white solid | 338 M⁺ | (CD₃OD)δ: 7.29 (1H, d, J = 8.1 Hz), 7.21 (1H, t, J = 7.9 Hz), 7.15 (1H, dd, J = 8.1, 1.8 Hz), 7.01 (1H, d, J = 1.8 Hz), 6.80-6.73 (3H, m), 3.84 (1H, q, J = 7.1 Hz), 3.07 (1H, dd, J = 13.6, 4.0 Hz), 2.54 (1H, dd, J = 13.6, 9.5 Hz), 2.47-2.26 (2H, m), 2.15-2.26 (2H, m), |

TABLE 1-continued

| No. | property | MS (m/Z) | ¹H-NMR (δ/ppm) |
|---|---|---|---|
| | | | 2.15-2.03 (2H, m), 2.00-1.90 (1H, m), 1.84-1.70 (1H, m), 1.68-1.52 (1H, m), 1.29 (3H, dd, J = 7.1, 1.6 Hz) |
| 21 | oil | 406 M⁺ | (CD₃OD)δ: 7.43 (2H, d, J = 8.8 Hz), 7.36-7.32 (3H, m), 7.20 (1H, d, J = 8.1 Hz), 7.04 (1H, s), 3.73 (1H, q, J = 7.2 Hz), 3.08 (1H, dd, J = 13.8, 4.0 Hz), 2.56 (1H, dd, J = 13.8, 9.2 Hz), 2.44-2.26 (2H, m), 2.15-1.94 (3H, m), 1.85-1.56 (2H, m), 1.30 (3H, d, J = 7.2 Hz) |
| 22 | oil | 352 M⁺ | (CD₃OD)δ: 7.31-7.22 (3H, m), 7.14 (1H, dd, J = 8.1, 1.8 Hz), 7.01-6.95 (3H, m), 3.86-3.79 (4H, m), 3.06 (1H, dd, J = 13.6, 4.0 Hz), 2.54 (1H, dd, J = 13.6, 9.2 Hz), 2.43-2.25 (2H, m), 2.15-1.58 (5H, m), 1.27 (3H, dd, J = 7.1, 1.3 Hz) |

TABLE 2

| No. | prpperty | MS (m/Z) | NMR (δ/ppm) |
|---|---|---|---|
| 23 | oil | 352 M⁺ | (CD₃OD)δ: 7.42 (2H, d, J = 8.1 Hz), 7.35-7.33 (3H, m), 7.17 (1H, d, J = 7.3 Hz), 7.04 (1H, s), 4.75 (2H, s), 3.87 (1H, q, J = 7.0 Hz), 3.16 (1H, dd, J = 13.7, 3.5 Hz), 2.51 (1H, dd, J = 13.9, 9.5 Hz), 2.40-2.30 (2H, m), 2.17-2.09 (2H, m), 2.02-1.92 (1H, m), 1.82-1.68 (1H, m), 1.63-1.50 (1H, m), 1.35 (3H, d, J = 7.0 Hz) |
| 24 | yellow solid | 368 M + H⁺ | (CD₃OD)δ: 8.27 (2H, d, J = 8.8, 0.9 Hz), 7.53 (2H, d, J = 8.8 Hz), 7.40 (1H, d, J = 8.1 Hz), 7.24 (1H, dd, J = 8.1, 1.8 Hz), 7.03 (1H, d, J = 1.8 Hz), 3.74 (1H, q, J = 7.1 Hz), 3.16 (1H, dd, J = 13.7, 3.8 Hz), 2.55 (1H, dd, J = 13.7, 9.5 Hz), 2.42-2.32 (2H, m), 2.20-1.95 (3H, m), 1.84-1.51 (2H, m), 1.37 (3H, d, J = 7.0 Hz) |
| 25 | brown solid | 337 M⁺ | (CDCl₃)δ: 7.31 (1H, d, J = 8.1 Hz), 7.15-7.10 (3H, m), 7.03 (1H, s), 6.73 (2H, d, J = 8.4 Hz), 4.68 (3H, s), 3.97 (1H, q, J = 7.1 Hz), 3.15 (1H, dd, J = 13.7, 3.5 Hz), 2.48 (1H, dd, J = 13.7, 9.9 Hz), 2.41-2.30 (2H, m), 2.18-1.95 (3H, m), 1.81-1.50 (2H, m), 1.35 (3H, d, J = 6.6 Hz) |
| 31 | oil | 322 M⁺ | (CD₃OD)δ: 7.44 (6H, m), 7.17 (1H, dd, J = 7.9, 2.0 Hz), 7.02 (1H, d, J = 1.8 Hz), 3.78 (1H, q, J = 7.2 Hz), 3.07 (1H, dd, J = 13.6, 4.0 Hz), 2.55 (1H, dd, J = 13.6, 9.2 Hz), 2.47-2.25 (2H, m), 2.13-1.72 (4H, m), 1.28 (3H, dd, J = 7.2, 1.3 Hz) |
| 32 | oil | 336 M⁺ | (CDCl₃)δ: 7.34 (1H, d, J = 8.1 Hz), 7.22 (4H, s), 7.15 (1H, d, J = 8.4 Hz), 7.04 (1H, s), 3.91 (1H, q, J = 7.1 Hz), 3.16 (1H, dd, J = 13.9, 3.7 Hz), 2.50 (1H, dd, J = 13.9, 9.5 Hz), 2.40 (3H, s), 2.37-2.28 (2H, m), 2.18-2.06 (3H, m), 1.99-1.93 (1H, m), 1.80-1.68 (1H, m), 1.59-1.31 (1H, m), 1.36 (3H, dd, J = 7.0, 1.1 Hz) |
| 33 | Oil | 368 M⁺ | (CDCl₃)δ: 7.36-7.26 (5H, m), 7.16 (1H, d, J = 8.1 Hz), 7.03 (1H, s), 3.90 (1H, q, J = 7.1 Hz), 3.16 (1H, dd, J = 13.7, 3.8 Hz), 2.55-2.47 (4H, m), 2.39-2.31 (2H, m), 2.18-2.09 (2H, m), 2.03-1.91 (1H, m), 1.88-1.70 (1H, m), 1.66-1.50 (1H, m), 1.36 (3H, dd, J = 7.1, 0.9 Hz) |
| 34 | Oil | 340 M⁺ | (CD₃OD)δ: 7.36-7.31 (3H, m), 7.20-7.12 (3H, m), 7.02 (1H, d, J = 1.8 Hz), 3.75 (1H, q, J = 7.1 Hz), 3.07 (1H, dd, J = 13.7, 4.2 Hz), 2.55 (1H, dd, J = 13.7, 9.5 Hz), 2.43-2.26 (2H, m), 2.15-2.03 (2H, m), 2.00-1.91 (1H, m), 1.86-1.68 (1H, m), 1.65-1.52 (1H, m), 1.29 (3H, dd, J = 7.1, 1.1 Hz) |

TABLE 3

| No. | property | MS (m/Z) | NMR (δ/ppm) |
|---|---|---|---|
| 35 | Oil | 366 M⁺ | (CDCl₃)δ: 8.10 (2H, d, J = 8.4 Hz), 7.42 (2H, d, J = 8.4 Hz), 7.36 (1H, d, J = 8.1 Hz), 7.18 (1H, d, J = 8.1 Hz), 7.01 (1H, s), 3.79 (1H, q, J = 7.3 Hz), 3.13 (1H, dd, J = 13.9, 9.5 Hz), 2.50 (1H, dd, J = 13.9, 9.5 Hz), 2.35-2.27 (2H, m), 2.14-2.05 (2H, m), |

TABLE 3-continued

| No. | property | MS (m/Z) | NMR (δ/ppm) |
|---|---|---|---|
| | | | 1.99-1.93 (1H, m), 1.75-1.65 (1H, m), 1.60-1.50 (1H, m), 1.36 (3H, d, J = 7.3 Hz) |
| 40a | Oil | 289 M$^+$ + Na | (CDCl$_3$)δ: 7.19 (1H, t, J = 7.9 Hz), 6.96 (1H, dd, J = 7.9, 1.6 Hz), 6.92 (1H, dd, J = 11.0, 1.5 Hz), 4.09 (1H, t, J = 3.5 Hz), 4.00 (1H, q, J = 7.2 Hz), 2.82 (1H, dd, J = 13.6, 7.7 Hz), 2.61 (1H, dd, J = 13.6, 7.7 Hz), 2.02-1.91 (1H, m), 1.89-1.77 (2H, m), 1.73-1.61 (2H, m), 1.60-1.43 (1H, m), 1.53-1.45 (1H, m), 1.50 (3H, d, J = 7.3 Hz) |
| 40c | white solid | 289 M$^+$ + Na | (CDCl$_3$)δ: 7.19 (1H, t, J = 7.9 Hz), 6.91-6.83 (2H, m), 3.99 (1H, q, J = 7.2 Hz), 3.87 (1H, q, J = 5.9 Hz), 2.77 (1H, dd, J = 13.9, 5.9 Hz), 2.39 (1H, dd, J = 13.6, 9.2 Hz), 1.92-1.58 (9H, m), 1.26-1.14 (1H, m) |
| 41a | Oil | 349 M$^+$ + Na | (CDCl$_3$)δ: 7.45 (1H, d, J = 1.5 Hz), 7.24 (1H, d, J = 7.7 Hz), 7.16 (1H, dd, J = 8.1, 1.5 Hz), 4.24 (1H, q, J = 7.2 Hz), 4.09 (1H, s), 2.82 (1H, dd, J = 13.7, 7.9 Hz), 2.61 (1H, dd, J = 13.7, 7.5 Hz), 2.00-1.80 (3H, m), 1.72-1.49 (7H, m) |
| 41c | Oil | 349 M$^+$ + Na | (CDCl$_3$)δ: 7.41 (1H, s), 7.25 (1H, d, J = 7.0 Hz), 7.11 (1H, d, J = 8.1 Hz), 4.23 (1H, q, J = 7.2 Hz), 3.89 (1H, q, J = 5.9 Hz), 2.76 (1H, dd, J = 13.7, 6.0 Hz), 2.42 (1H, dd, J = 13.9, 6.8 Hz), 2.09-1.92 (2H, m), 1.86-1.78 (1H, m), 1.71-1.47 (6H, m), 1.29-1.16 (1H, m) |
| 42 | white solid | 340 M$^+$ | (CD$_3$OD)δ: 7.26 (1H, d, J = 8.1 Hz), 7.15 (3H, d, J = 8.4 Hz), 7.04 (1H, s), 6.82 (2H, d, J = 8.4 Hz), 4.04 (1H, brs), 3.85 (1H, q, J = 7.1 Hz), 2.87 (1H, dd, J = 6.8, 3.4 Hz), 2.56 (1H, dd, J = 13.4, 8.2 Hz), 2.02-1.90 (2H, m), 1.27 (3H, d, J = 7.0 Hz) |
| 43 | White solid | 340 M$^+$ | (CD$_3$OD)δ: 7.27 (1H, d, J = 8.1 Hz), 7.15-7.12 (3H, m), 7.00 (1H, s), 6.83 (2H, d, J = 8.6 Hz), 3.86-3.81 (2H, m), 2.85 (1H, dd, J = 13.6, 5.5 Hz), 2.38 (1H, dd, J = 13.5, 9.2 Hz), 2.00 (1H, d, J = 28.9 Hz), 1.90 (1H, d, J = 25.8 Hz), 1.60-1.78 (4H, m), 1.27 (4H, d, J = 7.0 Hz) |

The above-mentioned loxoprofen derivative provided by the present invention may be used as it is, that is, as a free carboxylic acid, or as a pharmacologically acceptable salt thereof.

Pharmacologically acceptable salts may include alkali metal salts such as a sodium salt and a potassium salt or ammonium salts.

When the loxoprofen derivative provided by the present invention or a pharmacologically acceptable salt thereof is administered as a pharmaceutical composition, for example, the derivative or the pharmacologically acceptable salt thereof as an active ingredient may be administered orally or parenterally alone or in a suitable dosage form, such as a capsule, a tablet, and an injection, in conjunction with a conventional excipient. Specifically, for example, a capsule may be formulated by mixing a loxoprofen derivative or a salt thereof with an excipient such as lactose, starch or a derivative thereof, and a cellulose derivative and filling the mixture into a gelatine capsule.

A tablet may be formulated by adding a binding agent such as sodium carboxymethylcellulose, alginic acid, or gum arabic and water in addition to the above-mentioned excipient and kneading the mixture, granulating it if necessary, then further adding a lubricant such as talc or stearic acid, and using a normal tablet compressing machine.

Furthermore, in the case of a parenteral administration by injection, an injectable formulation is formulated by dissolving a loxoprofen derivative or a salt thereof together with a solubilizer in sterile distilled water or sterile saline, and placing the solution into an ampoule and sealing the ampoule. If necessary, a stabilizing agent, a buffering agent, and the like may be included. These formulations for parenteral administration may be administered by intravenous administration or an intravenous infusion.

The dosage of the loxoprofen derivative provided by the present invention varies depending on various factors such as the symptom of the patient to be treated, the patient's severity, the patient's age, and the presence or absence of a complication, and thus, the dosage is not always the same.

The dosage also varies depending on an administration route, a dosage form, the frequency of administration, and the like; however, in general, the loxoprofen derivative as an active ingredient may be administered in a dosage selected as follows: in the case of oral administration, the dosage may be usually selected within 0.1 to 1000 mg/day/person, preferably within 1 to 500 mg/day/person as appropriate; and in the case of parenteral administration, the dosage may be selected within about 1/100 to 1/2 amount of the dosage for the oral administration as appropriate. Naturally, these dosages may be increased or decreased if necessary depending on the patient's age, symptoms, and the like.

EXAMPLES

Hereinbelow, the present invention will be described more specifically with reference to Test Examples instead of Working Examples, but it is needless to say that the scope of the present invention is not intended to be limited to these examples.

The chemical structure of the loxoprofen derivative of the present invention used in an in vitro test and in vivo test is shown below.

[Chemical Formula 11]

TABLE 4

| TEST COMPOUND | COMPOUND NUMBER | R[20] |
|---|---|---|
| loxoprofen | — | H |
| Compound 1 | 9a | F |
| Compound 2 | 9c | Br |
| Compound 3 | 19 | p-hydroxyphenyl- |
| Compound 4 | 25 | p-aminophenyl- |

Test Example 1

Human Whole Blood Assay (In Vitro)

This test was performed according to the method described in Inflamm. Res., 45: 68-74 (1996).
A: In Vitro COX-1 Assay A person who had not taken NSAIDs for at least one week and was healthy on the day of blood collection was selected as a subject for blood collection.

Blood was collected without adding an anticoagulant agent and used for the assay immediately. The collected blood was dispensed in 500 μL aliquots into tubes (Protein Lobingdin tube, Eppenduf Co. LTD., Tokyo, Japan). Two μL of the test compound (final concentration: 0.1 μM to 1000 μM) dissolved in an appropriate solvent (DMSO or MilliQ water) was added and incubated at 37° C. for 24 hours until blood coagulation was observed.

After incubation, the samples were centrifuged at 12,000×g for 5 minutes to separate serum. 100 μL of the obtained serum was added to 400 μL of ethanol to remove blood protein and centrifuged again at 12,000×g for 5 minutes. $TXB_2$ in the supernatant was quantified by using an enzyme immunoassay (EIA) kit [Cayman (Ann, Arbor, Mich., USA) #519031]. The protocol followed the protocol attached to the kit.
B: In Vitro COX-2 Assay A person who had not taken NSAIDs for at least one week and was healthy on the day of blood collection was selected as a subject for blood collection.

Blood was collected in heparin-treated test tubes (Venojectll blood collection tubes, Terumo Corporation), and an inflammatory stimulant, lipopolysaccharide (LPS) (Sigma-Aldrich Japan Inc., #L2880 from E. coli055:B5: diluted in phosphate buffered saline (PBS) to a final concentration of 100 μg/mL) was added to the blood. The mixture was dispensed in 500 μL aliquots into tubes. 2 μL of the test compound (final concentration: 0.1 μM to 1000 μM) dissolved in an appropriate solvent (DMSO or MilliQ water) was added and incubated at 37° C. for 24 hours to induce COX-2.

After incubation, the samples were centrifuged at 12,000×g for 5 minutes to separate serum. 100 μL of the obtained serum was added to 400 μL of ethanol to remove blood protein, and the mixture was centrifuged again at 12,000×g for 5 minutes. PGE2 in the supernatant was quantified by using an enzyme immunoassay (EIA) kit [Cayman (Ann, Arbor, Mich., USA) #514040]. The protocol followed the protocol attached to the kit.

Test Example 2

Renal Damage Assay (In Vivo)

This test was performed according to the method described in Biochem. Biophysical. Res. Com., 323; 1032-39 (2004).
A: Preparation Method of Liposomal Membrane Egg yolk phosphatidylcholine (10 μM, 7.7 mg: manufactured by KANTO CHEMICAL CO., INC.) was dissolved in chloroform/methanol (1:2, v/v), dried, and then dissolved in 1.5 mL of diethylether. 1 mL of 100 mM calcein-NaOH (pH 7.4) was added to the solution and the mixture was sonicated for 1 minute. Then, diethylether was removed by a conventional rotary evaporator (25° C.) and the residue was suspended in phosphate buffer to obtain solution of liposomal membrane (reversed-phase evaporation method).
B: Membrane Injury Assay (1) Assay Using Water as a Solvent 30 μL of the liposomal membrane solution was suspended in 5 mL of phosphate buffer, and the suspension was centrifuged (at 10,500×g for 20 minutes) and washed with phosphate buffer twice. The pellet was suspended in 1 mL of phosphate buffer and the suspension was used for a membrane injury experiment.

The suspension was dispensed in 6 μL aliquots into 1.5 mL tubes. 6 μL of test samples at different concentrations in phosphate buffer were added to the liposome suspensions and incubated at 30° C. for 10 minutes. After cooling on ice, the mixed solution was dispensed in 10 μL aliquots into each well of a 384-well plate, and then the fluorescence intensity of leaked calcein was measured (excitation wavelength: 490 nm).

(2) Assay Using DMSO as a Solvent

The liposome suspension was centrifuged (at 10,500×g for 20 minutes) and washed with phosphate buffer twice. The pellet was suspended in 5 mL of phosphate buffer, and 0.75 mL of the suspension was diluted with 50 mL of phosphate buffer and used for the membrane injury experiment.

The diluted suspension was dispensed in 400 μL aliquots into 1.5 mL tubes. Test sample solutions at different concentrations in DMSO were added to the liposome suspensions and incubated at 30° C. for 10 minutes. After cooling on ice, the mixed solution was dispensed in 200 μL aliquots into each well of a 96-well plate, and then the fluorescence intensity of leaked calcein was measured (excitation wavelength: 490 nm).
C: Evaluation of Ability to Cause Membrane Injury A 25% solution of triton X-100 was used as a control and the membrane injury caused by this solution was considered as 100% membrane injury. After measuring the fluorescence intensity caused by each test sample, the ratio of the fluorescence intensity to that of the control considered as 100% membrane injury was expressed as a percentage and this was used as an index of the ability to cause membrane injury (calcein release).

These results are collectively shown in the table below.

TABLE 5

| TEST COMPOUND | COX INHIBITORY ACTIVITY IC$_{50}$ (mM) COX. 1 | COX. 2 | COX-2 SELECTIVITY COX. 1/COX. 2 | MEMBRANE INJURY Calcein release ED$_{50}$ % (nM) |
|---|---|---|---|---|
| LOXONIN | 36 | 9 | 4.0 | 800 |
| Compound 1 | 16 | 6 | 2.0 | >1,000 |
| Compound 2 | 9.9 | 16 | 0.6 | >1,000 |
| Compound 3 | 570 ± 80 | 21 ± 13 | 40 ± 21 | 15 |
| Compound 4 | 675 ± 64 | 85 ± 9 | 8.0 | >1,000 |

Test Example 3

Assay Using an Animal (In Vivo Test)

A: Formation of a Gastric Ulcer Induced by a Loxoprofen Derivative

This test was performed according to the method described in Biochem. Pharmacol., 67; 575-85 (2004).

After male Wister rats (body weight: 180 to 200 g) were fasted for 18 hours, test compounds were administered orally to them (the dosage was determined so that an amount of substance of a test compound is equal to loxoprofen). After 8 hours, the stomach was excised and the area of the ulcers that developed inside the stomach was measured. The total area of all the ulcers was used as an ulcer index.

On the other hand, the amount of PGE$_2$ in the gastric mucosae was measured by an ELISA method.

The protocol followed the protocol attached to the kit.

Figure 1:
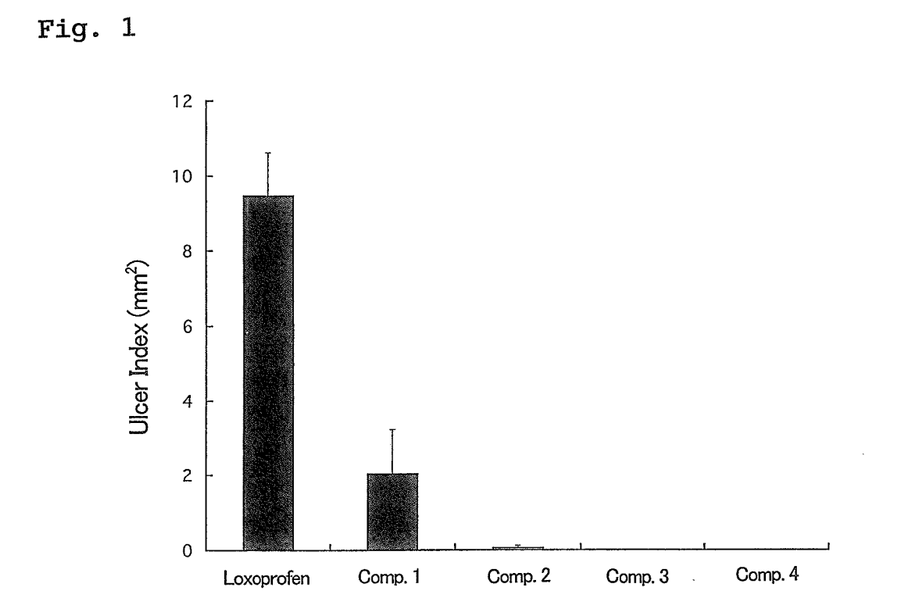
FIG. 1 is a diagram showing the results of an ulcer index measurement in Test Example 3 in which compounds were administered in an amount equivalent to 40 mg/kg of loxoprofen.
Figure 2:
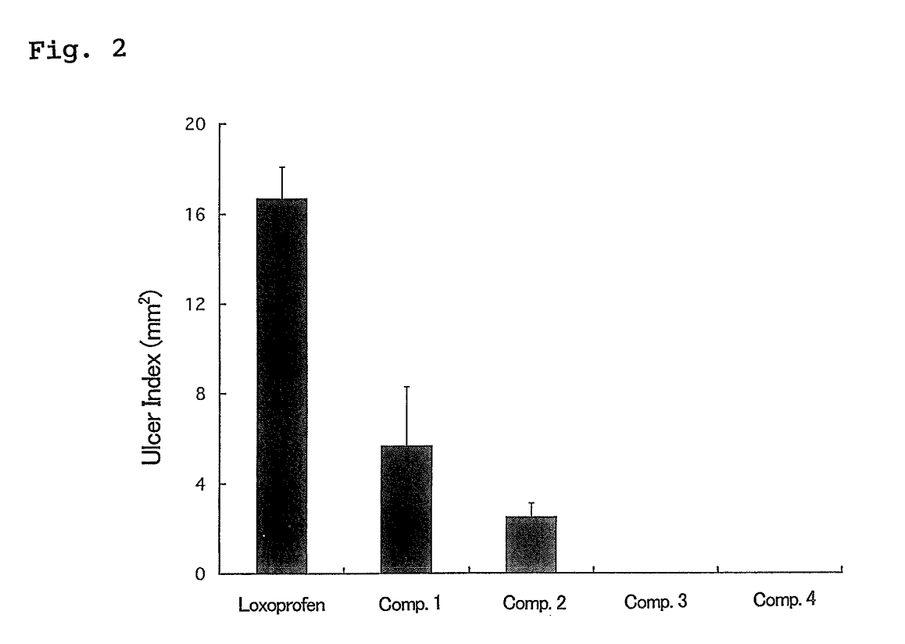
FIG. 2 is a diagram showing the results of an ulcer index measurement in Test Example 3 in which compounds were administered in an amount equivalent to 50 mg/kg of loxoprofen.
Figure 3:
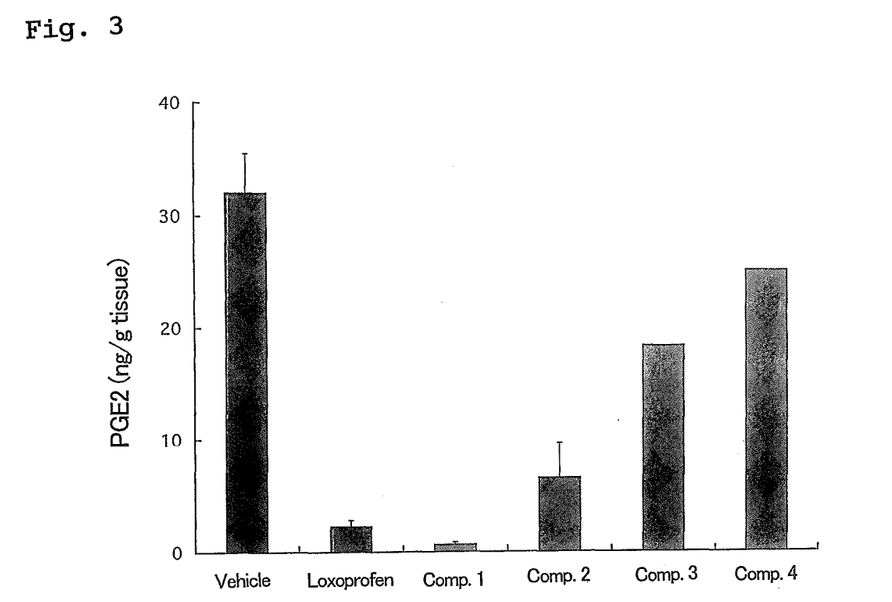
FIG. 3 is a diagram showing the change in the amount of the gastric mucosa $PGE_2$ in Test Example 3 in which compounds were administered in an amount equivalent to 40 mg/kg of loxoprofen.

These results are shown in FIGS. 1 to 3.

FIG. 1 shows the results when the test compounds were administered in an amount equivalent to 40 mg/kg of loxoprofen. FIG. 2 shows the results when the test compounds were administered in an amount equivalent to 50 mg/kg of loxoprofen. FIG. 3 shows the change in the amount of the gastric mucosa PGE$_2$.

As is found from the results shown in the figures, the loxoprofen derivatives of the present invention (Compounds 1 to 4) have significantly less ulcer indices than loxoprofen. Formation of an ulcer was hardly observed when Compound 3 or Compound 4 was used.

The amount of the gastric mucosa PGE$_2$ when Compound 2, Compound 3, or Compound 4 was used was more than that when loxoprofen was used.

B: Effect of a Loxoprofen Derivative on Carrageenan-Induced Edema

This test was performed according to the method described in Br. J. Pharmacol., 151; 285-91 (2007).

After male Wister rats (body weight: 180 to 200 g) were fasted for 18 hours, test compounds were administered orally to them (the dosage was determined so that an amount of substance of a test compound is equal to loxoprofen). After 1 hour, rats were injected subcutaneously with 100 μL of 1% carrageenin (dissolved in saline) in their left footpads to induce edema.

The paw volumes were measured before and 3 hours and 6 hours after administration of carrageenin by Plethysmometer.

PGE$_2$ in paw edema was also measured by an ELISA method. The protocol followed the protocol attached to the kit.

Figure 4:
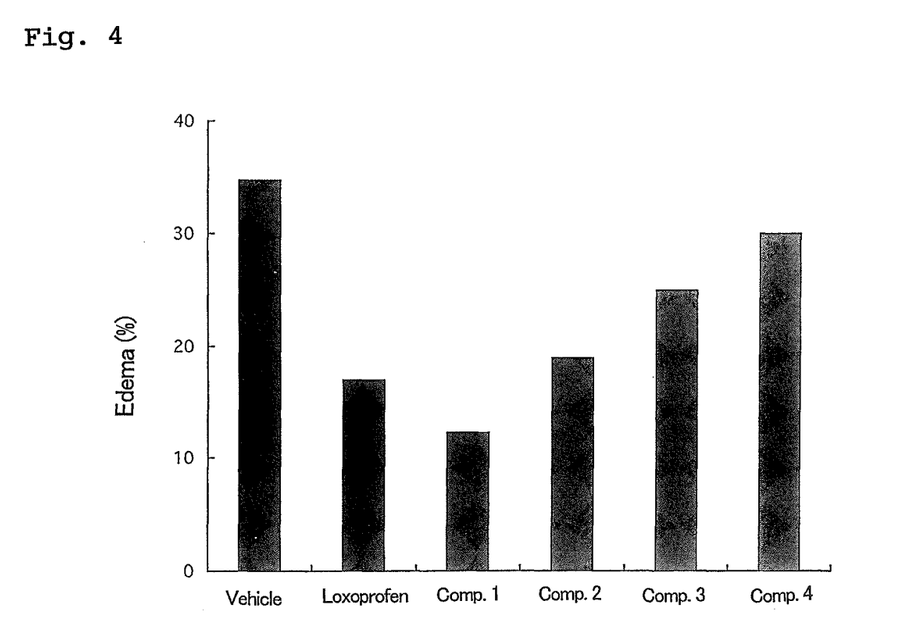
FIG. 4 is a diagram showing the percentage of carrageenan-induced edema (%) 6 hours after administration of test compounds in an amount equivalent to 10 mg/kg of loxoprofen in Test Example 3.
Figure 5:
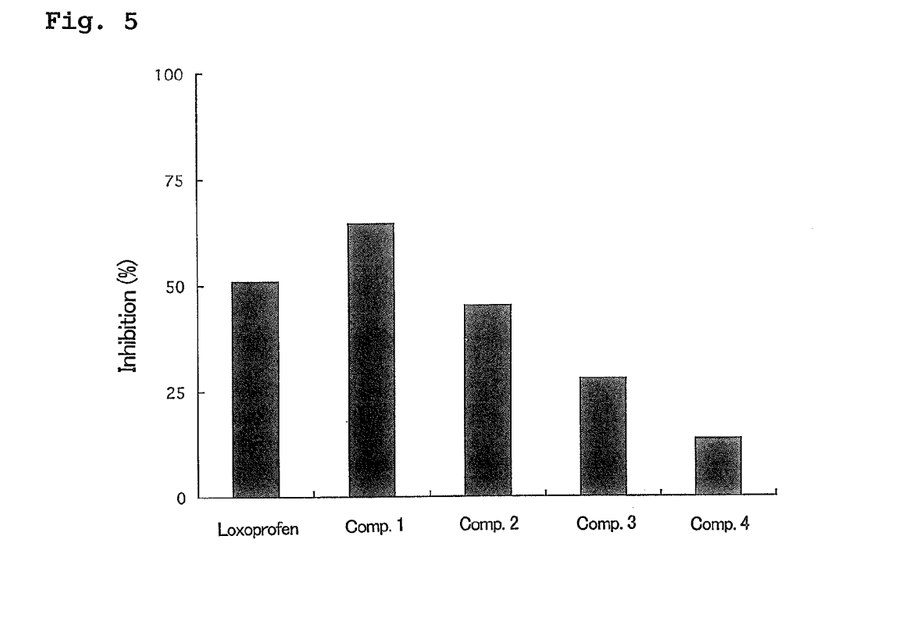
FIG. 5 is a diagram showing the percentage of inhibition of carrageenan-induced edema (%) 6 hours after administration of test compounds in an amount equivalent to 10 mg/kg of loxoprofen in Test Example 3.
Figure 6:
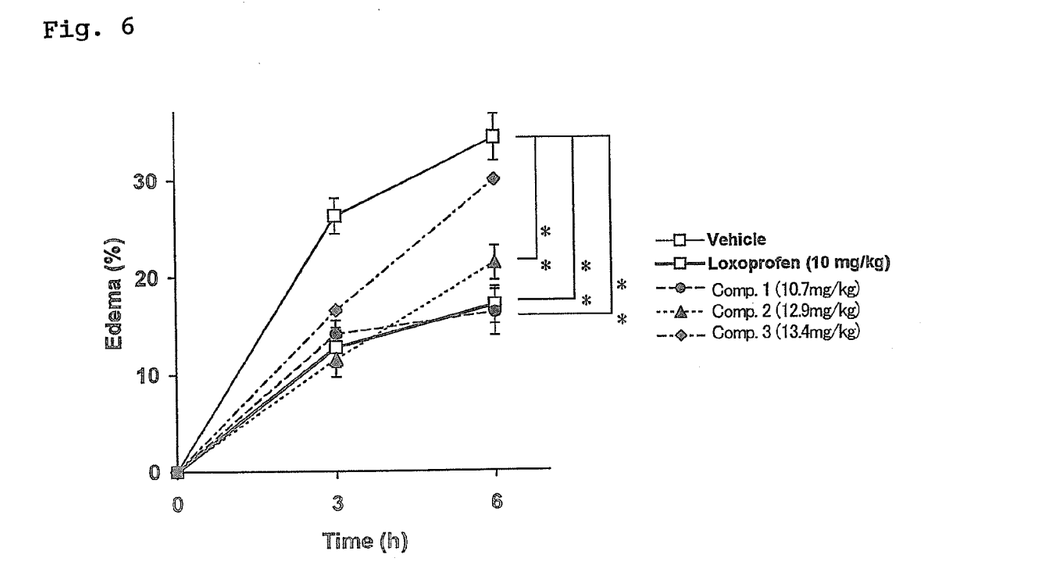
FIG. 6 is a diagram showing the change in the paw volumes 3 hours and 6 hours after administration of test compounds in an amount equivalent to 10 mg/kg of loxoprofen in Test Example 3.

These results are shown in FIGS. 4 to 6.

FIG. 4 shows the percentage of carrageenan-induced edema (%) 6 hours after administration of test compounds in an amount equivalent to 10 mg/kg of loxoprofen, and FIG. 5 shows the percentage of inhibition of edema (%) 6 hours after administration of test compounds in an amount equivalent to 10 mg/kg of loxoprofen.

The percentage of inhibition of edema was calculated based on the formula below:

The percentage of inhibition (%)=100−(the edema volume when a compound was administered/the edema volume when a vehicle was administered)×100.

FIG. 6 shows the change in the paw volumes 3 hours and 6 hours after administration.

As is found from these results, the loxoprofen derivatives of the present invention (Compounds 1 to 4) have a good antiphlogistic effect and also do not cause formation of an ulcer, which is a side effect. The loxoprofen derivatives of the invention are found to be compounds in which their pharmacological effects were successfully separated from their side effects.

Exemplary Formulation 1: Tablet

| Compound 1 | 50 mg |
|---|---|
| Lactose | 100 mg |
| Hydroxypropylcellulose | 150 mg |
| magnesium stearate | 50 mg |

Based on the formulation described above, granules were prepared and compressed to produce tablets weighing 350 mg by a conventional method.

Exemplary Formulation 2: Granule

| Compound 2 | 50 mg |
|---|---|
| Lactose | 100 mg |
| corn starch | 150 mg |

Based on the formulation described above, granules that contained 50 mg of active ingredient in 200 mg of granules were prepared by a conventional method.

INDUSTRIAL APPLICABILITY

As described above, the loxoprofen derivative provided by the present invention is a novel compound that has been unknown until now. Furthermore, the loxoprofen derivative provided by the invention has no side effect such as a gastrointestinal disorder, which is caused by conventional NSAIDs, and moreover has stronger anti-inflammatory and analgesic effects than clinically-used loxoprofen.

Therefore, the loxoprofen derivative provided by the invention is very effective in that it can be used safely in humans due to its wide safety margin and contributes greatly to the industry.

The invention claimed is:

1. A loxoprofen derivative represented by the following formula (I) or (II):

[Chemical Formula 1]

(I)

-continued (II)

wherein R¹ and R² each represent a halogen atom or a substituted or unsubstituted phenyl group or a pharmacologically acceptable salt thereof.

2. The loxoprofen derivative or a pharmacologically acceptable salt thereof according to claim 1, wherein the halogen atom represented by R¹ and R² in the formulae (I) and (II) is selected from a chlorine atom, a bromine atom, a fluorine atom, and an iodine atom.

3. The loxoprofen derivative or a pharmacologically acceptable salt thereof according to claim 1, wherein a substituent of the substituted phenyl group represented by R¹ in the formula (I) is a halogen atom, a hydroxyl group, a substituted or unsubstituted lower alkyl group, a lower alkylthio group, a lower alkoxy group, a nitro group, an amino group, or a carboxyl group.

4. The loxoprofen derivative or a pharmacologically acceptable salt thereof according to claim 1, wherein a substituent of the substituted phenyl group represented by R² in the formula (II) is a halogen atom or a substituted lower alkyl group.

5. A pharmaceutical preparation, comprising the loxoprofen derivative represented by the formula (I) or (II) or the pharmacologically acceptable salt thereof according to claim 1 as an active ingredient.

6. A pharmaceutical preparation, comprising the loxoprofen derivative or the pharmacologically acceptable salt thereof according to claim 2 as an active ingredient.

* * * * *